(12) United States Patent
Murata et al.

(10) Patent No.: US 11,247,027 B2
(45) Date of Patent: Feb. 15, 2022

(54) GUIDEWIRE HAVING A DISTAL-END BRAZING MEMBER FORMED WITH DIFFERENT BRAZING PORTIONS

(71) Applicant: ASAHI INTECC CO., LTD., Seto (JP)

(72) Inventors: Satoru Murata, Seto (JP); Tadahiro Koike, Ama (JP); Yumiko Nakagawa, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 581 days.

(21) Appl. No.: 15/870,018

(22) Filed: Jan. 12, 2018

(65) Prior Publication Data

US 2018/0133439 A1 May 17, 2018

Related U.S. Application Data

(62) Division of application No. 14/739,349, filed on Jun. 15, 2015, now abandoned.

(30) Foreign Application Priority Data

Sep. 16, 2014 (JP) .................. 2014-187257

(51) Int. Cl.
*A61M 25/09* (2006.01)

(52) U.S. Cl.
CPC ... *A61M 25/09* (2013.01); *A61M 2025/09083* (2013.01); *A61M 2025/09133* (2013.01)

(58) Field of Classification Search
None
See application file for complete search history.

(56) References Cited

U.S. PATENT DOCUMENTS

| 3,625,200 | A | | 12/1971 | Muller |
| 4,721,117 | A | | 1/1988 | Mar et al. |
| 4,940,062 | A | | 7/1990 | Hampton et al. |
| 5,144,959 | A | * | 9/1992 | Gambale ............... A61M 25/09 600/434 |

(Continued)

FOREIGN PATENT DOCUMENTS

| EP | 2 481 440 A1 | 8/2012 |
| EP | 2 532 382 A1 | 12/2012 |

(Continued)

OTHER PUBLICATIONS

Apr. 24, 2018 Office Action issued in Japanese Patent Application No. 2017-139795.

(Continued)

*Primary Examiner* — Matthew Kremer
(74) *Attorney, Agent, or Firm* — Oliff PLC

(57) ABSTRACT

A guidewire has a distal-most end portion that retains its desired shape. The guidewire includes a first brazing member joining a distal end of a core shaft to a distal end of an outer coil, and a second brazing member provided adjacent to and on a proximal side of the first brazing member. The guidewire also includes an outer coil surrounding an outer periphery of the core shaft, and an inner coil provided between the outer coil and the core shaft. The second brazing member is provided between the outer coil and the inner coil, but is not provided between the inner coil and the core shaft. The melting point of the first brazing member is higher than the melting point of the second brazing member.

8 Claims, 4 Drawing Sheets

(56) References Cited

U.S. PATENT DOCUMENTS

| | | | |
|---|---|---|---|
| 5,228,453 A | 7/1993 | Sepetka | |
| 5,345,945 A * | 9/1994 | Hodgson | A61M 25/09033 600/433 |
| 5,725,534 A | 3/1998 | Rasmussen | |
| 5,776,080 A | 7/1998 | Thome et al. | |
| 5,916,166 A | 6/1999 | Reiss et al. | |
| 7,316,656 B2 * | 1/2008 | Shireman | A61M 25/09 600/585 |
| 2006/0122537 A1 | 6/2006 | Reynolds et al. | |
| 2009/0036832 A1 * | 2/2009 | Skujins | A61M 25/09 604/164.01 |
| 2009/0082800 A1 * | 3/2009 | Janardhan | A61F 2/013 606/200 |
| 2011/0160703 A1 * | 6/2011 | Matsumoto | A61M 25/09 604/528 |
| 2012/0041420 A1 * | 2/2012 | Nagano | A61M 25/09 604/528 |
| 2012/0265100 A1 * | 10/2012 | Maki | A61M 25/09 600/585 |
| 2013/0289445 A1 * | 10/2013 | Edamatsu | A61M 25/09 600/585 |
| 2014/0350568 A1 * | 11/2014 | Shekalim | A61B 17/22 606/127 |

FOREIGN PATENT DOCUMENTS

| | | |
|---|---|---|
| GN | 103372261 A | 10/2013 |
| JP | 2009-190055 | 8/2009 |
| JP | 2012-034967 A | 2/2012 |
| JP | 2013-085854 A | 5/2013 |
| JP | 2013-111320 A | 6/2013 |
| JP | 2013-208351 A | 10/2013 |
| JP | 2014-136047 A | 7/2014 |
| WO | 98/42399 A1 | 10/1998 |

OTHER PUBLICATIONS

Aug. 24, 2018 Office Action issued in Chinese Patent Application No. 201510347706.X.
Feb. 12, 2 016 Office Action issued in European Patent Application No. 15172028.1.
May 23, 2017 Office Action issued in Japanese Patent Application No. 2014-187257.
U.S. Appl. No. 14/739,349, filed Jun. 15, 2 015 in the name of Murata et al.
Dec. 12, 2016 Office Action issued in U.S. Appl. No. 14/739,349.
Nov. 1, 2017 Office Action issued in U.S. Appl. No. 14/739,349.
May 4, 2017 Office Action issued in U.S. Appl. No. 14/739,349.

* cited by examiner

GUIDEWIRE HAVING A DISTAL-END BRAZING MEMBER FORMED WITH DIFFERENT BRAZING PORTIONS

CROSS REFERENCE TO RELATED APPLICATION

This is a Division of application Ser. No. 14/739,349 filed Jun. 15, 2015, which claims priority to Japanese Application No. 2014-187257 filed on Sep. 16, 2014. The disclosure of the prior applications is hereby incorporated by reference herein in its entirety.

BACKGROUND

The disclosed embodiments relate to a guidewire to be inserted into a lumen such as blood vessels.

Guidewires for use at the time of inserting a catheter into a blood vessel are known. Insertion of the catheter is conducted by inserting the guidewire into a blood vessel first and then advancing the catheter over the guidewire. The guidewire thus is used as a guide to introduce the catheter to or into a lesion.

A guidewire used in such applications generally comprises a core shaft and a coil surrounding an outer periphery of the core shaft (a so-called coiled guidewire). In the coiled guidewire, a distal end of the core shaft and a distal end of the coil are joined to each other with a brazing material and, as a result, a distal-end brazing member is formed.

Because of, for example, reasons related to procedures when the guidewire is assembled, the distal-end brazing member is sometimes formed to include different portions, namely a distal-most end portion and a contiguous portion (formed by soldering) that is provided adjacent to and on a proximal side of the distal-most end portion (see Japanese Patent Application Publication No. 2014-136047 (JP-A-2014-136047), for example).

SUMMARY

However, such a conventional guidewire has a problem in that the distal-most end portion may be deformed due to a heat produced during soldering. Performance of the guidewire (passability in a lesion, for example) is influenced significantly by a shape of the distal-most end portion. Therefore, even when the distal-end brazing member of a guidewire is formed to include different portions, namely the distal-most end portion and the contiguous portion (formed by soldering) that is provided adjacent to and on the proximal side of the distal-most end portion, the distal-most end portion is required to retain its desired shape.

The disclosed embodiments have been devised to address such a problem in conventional techniques. An object of embodiments is to provide a guidewire in which, even though a distal-end brazing member of the guidewire is formed to include different portions, namely a first brazing member being provided at a distal-most end of the guidewire and a second brazing member being provided adjacent to the first brazing member, the first brazing member of the guidewire retains its desired shape reliably.

In order to achieve the above and/or other objects, a guidewire of embodiments adopts the following configuration. The guidewire includes:

a core shaft,
an outer coil surrounding an outer periphery of the core shaft,
a first brazing member that joins a distal end of the core shaft to a distal end of the outer coil, and
a second brazing member provided adjacent to and on a proximal side of the first brazing member. In addition, a melting point of the first brazing member is higher than a melting point of the second brazing member.

In the guidewire of embodiments, because the melting point of the first brazing member is higher than the melting point of the second brazing member that is adjacent to and on the proximal side of the first brazing member, deformation of the shape (hemispherical or arrowhead-like, for example) of the first brazing member due to a heat produced during formation of the second brazing member is prevented or minimized. Therefore, even when the distal-end brazing member of the guidewire is formed to include different portions, namely the first brazing member and the second brazing member, because of reasons related to procedures in assembling the guidewire, for example, the first brazing member at the distal-most end retains its desired shape reliably.

The guidewire may further include an inner coil provided between the outer coil and the core shaft, and the second brazing member may be provided between the outer coil and the inner coil but is not provided between the inner coil and the core shaft.

In the present guidewire, because the melting point of the first brazing member is higher than the melting point of the second brazing member, the first brazing member at the distal-most end retains its desired shape reliably.

In a guidewire having outer and inner coils, the second brazing member is thus provided between the outer coil and the inner coil but is not provided between the inner coil and the core shaft, and, as a result, an amount of a brazing material used for forming the second brazing member is reduced. For this reason, along with the relationship that the melting point of the first brazing member is higher than the melting point of the second brazing member, deformation of the first brazing member due to the heat produced during formation of the second brazing member is prevented or minimized reliably.

In the present guidewire, the first brazing member may be formed of a brazing material containing gold, silver and tin.

The brazing material containing gold, silver and tin has a melting point higher than a melting point of a gold-tin brazing material or a silver-tin brazing material that is commonly used in a guidewire. Therefore, by forming the first brazing member with the brazing material containing gold, silver and tin, deformation of the first brazing member due to the heat produced during formation of the second brazing member (formed of a gold-tin brazing material or a silver-tin brazing material) is prevented or minimized more reliably.

The present guidewire may include a curved part at a distal part of the guidewire, and the second brazing member may be provided in the curved part.

In such a guidewire, the presence of the second brazing member in the curved part enables retention of the curved shape of the guidewire. In addition, even though the second brazing member is provided in order to retain the curved shape of the guidewire, the first brazing member still retains its desired shape because the melting point of the first brazing member is higher than the melting point of the second brazing member. Thus, the guidewire simultaneously retains the desired curved shape of the guidewire and the desired shape of the first brazing member at the distal-most end.

DETAILED DESCRIPTION OF THE EMBODIMENTS

Various embodiments of a guidewire according to aspects of the present invention will be explained below.

Figure 1:
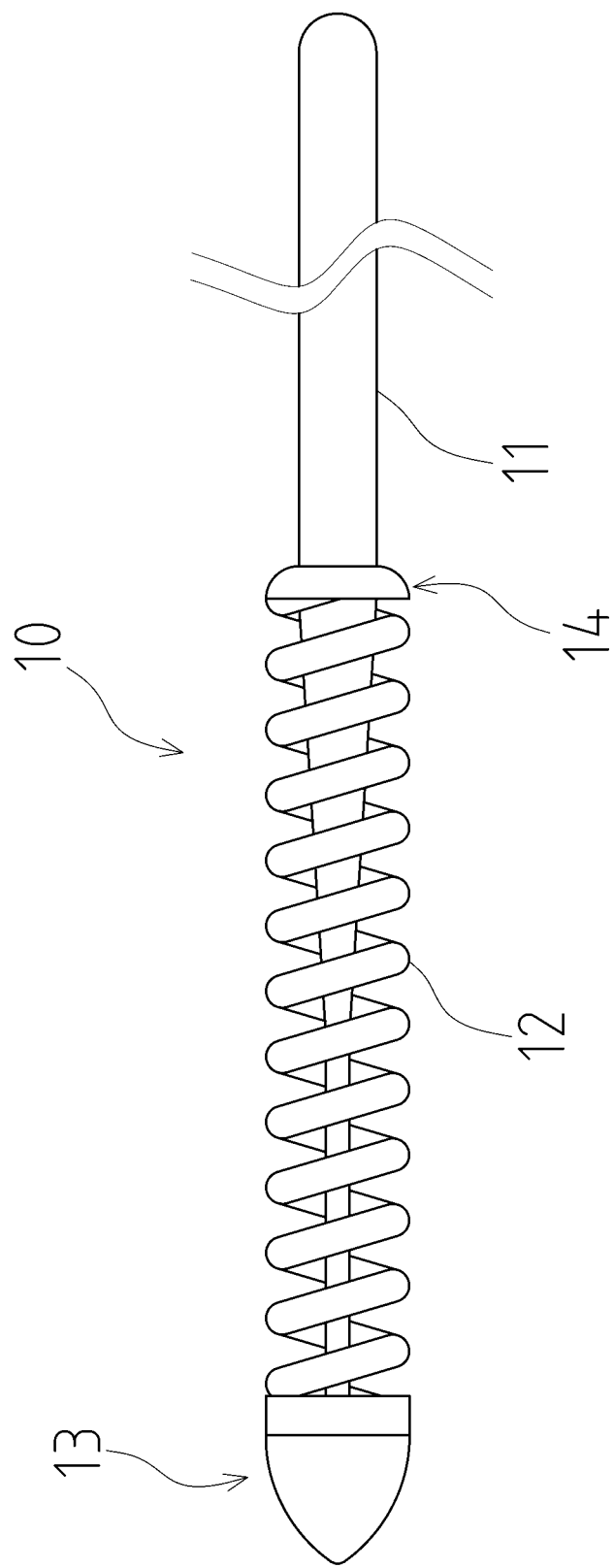
FIG. 1 is an explanatory view of a configuration of a guidewire according to the disclosed embodiments.

FIG. 1 is an explanatory view of a configuration of a guidewire 10 according to an embodiment of the present invention. The guidewire 10 includes a core shaft 11 and an outer coil 12 surrounding an outer periphery of the core shaft 11. The core shaft 11 and the outer coil 12 are joined to each other with a brazing material. In this embodiment, a distal end of the core shaft 11 and a distal end of the outer coil 12 are connected to each other with a distal-end brazing member 13, and a middle part of the core shaft 11 and a proximal end of the outer coil 12 are connected to each other with a proximal-end brazing member 14.

Figure 2:
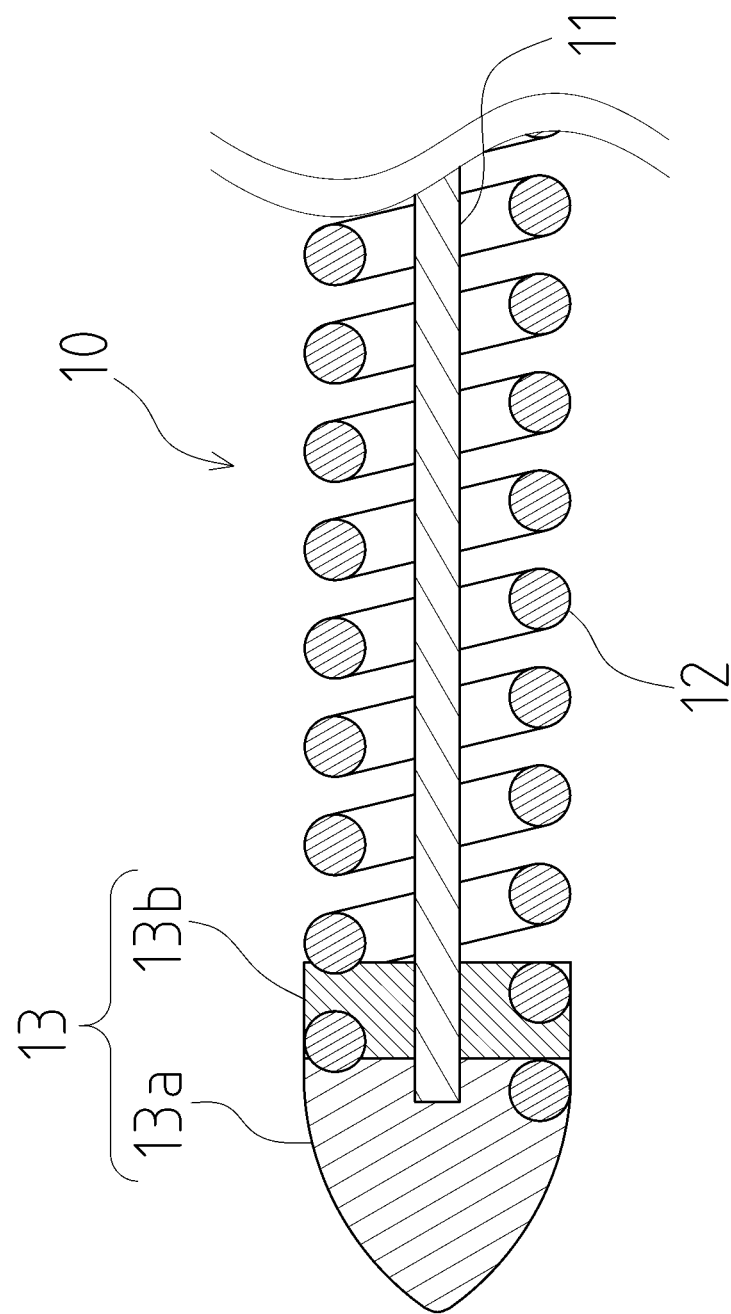
FIG. 2 is an explanatory view of a structure of a distal part of the guidewire according to the FIG. 1 embodiment.

FIG. 2 is an explanatory view of a structure of a distal part of the guidewire 10 of FIG. 1. As shown in FIG. 2, in the guidewire 10 of this embodiment, the distal-end brazing member 13 for joining the distal end of the core shaft 11 to the distal end of the outer coil 12 consists of two portions. The distal-end brazing member 13 consists of a first brazing member 13a located at a distal-most end of the guidewire 10 and a second brazing member 13b located adjacent to and on a proximal side of the first brazing member 13a.

In the guidewire 10, the distal end of the core shaft 11 and the distal end of the outer coil 12 are brazed to each other first, and then, after the brazing material solidifies, the brazing member is processed so as to form the first brazing member 13a that is pointed toward the distal side (an arrowhead-like shape). Subsequently, a brazing material is applied to an area adjacent to and on the proximal side of the first brazing member 13a to form the second brazing member 13b.

In the guidewire 10, a melting point of a brazing material A forming the first brazing member 13a is higher than a melting point of a brazing material B forming the second brazing member 13b. Examples of combinations of the brazing material A and the brazing material B include the following combinations.

(Combination 1)

Brazing material A: a brazing material containing gold, silver and tin, and

Brazing material B: a gold-tin brazing material (Combination 2)

Brazing material A: a brazing material containing gold, silver and tin, and

Brazing material B: a silver-tin brazing material (Combination 3)

Brazing material A: a gold-tin brazing material, and

Brazing material B: a silver-tin brazing material

In the guidewire 10 of this embodiment, the brazing material A used for forming the first brazing member 13a is a brazing material containing gold, silver and tin, and the brazing material B used for forming the second brazing member 13b is a gold-tin brazing material.

In the guidewire 10, because the melting point of the first brazing member 13a is higher than the melting point of the second brazing member 13b adjacent to the first brazing member 13a, deformation of the first brazing member 13a due to the heat produced during formation of the second brazing member 13b is prevented.

Performance of the guidewire (passability in a lesion, for example) is influenced significantly by the shape of the distal-most end portion of the guidewire 10. In this regard, the guidewire 10 is excellent in that the first brazing member 13a that has significant effect on the performance of the guidewire 10 retains its desired shape reliably even when the distal-end brazing member 13 is formed to include different parts, namely the first brazing member 13a and the second brazing member 13b, for reasons related to procedures in assembling, for example.

In addition, in the guidewire 10, the brazing material A used for forming the first brazing member 13a is the brazing material containing gold, silver and tin. The brazing material containing gold, silver and tin has a melting point (about 400° C.) higher than the melting point of a gold-tin brazing material or a silver-tin brazing material (200 to 300° C.) that is commonly used in a guidewire. Therefore, by forming the first brazing member 13a with the brazing material containing gold, silver and tin, deformation of the first brazing member 13a due to the heat produced during formation of the second brazing member 13b is prevented more reliably.

Figure 3:
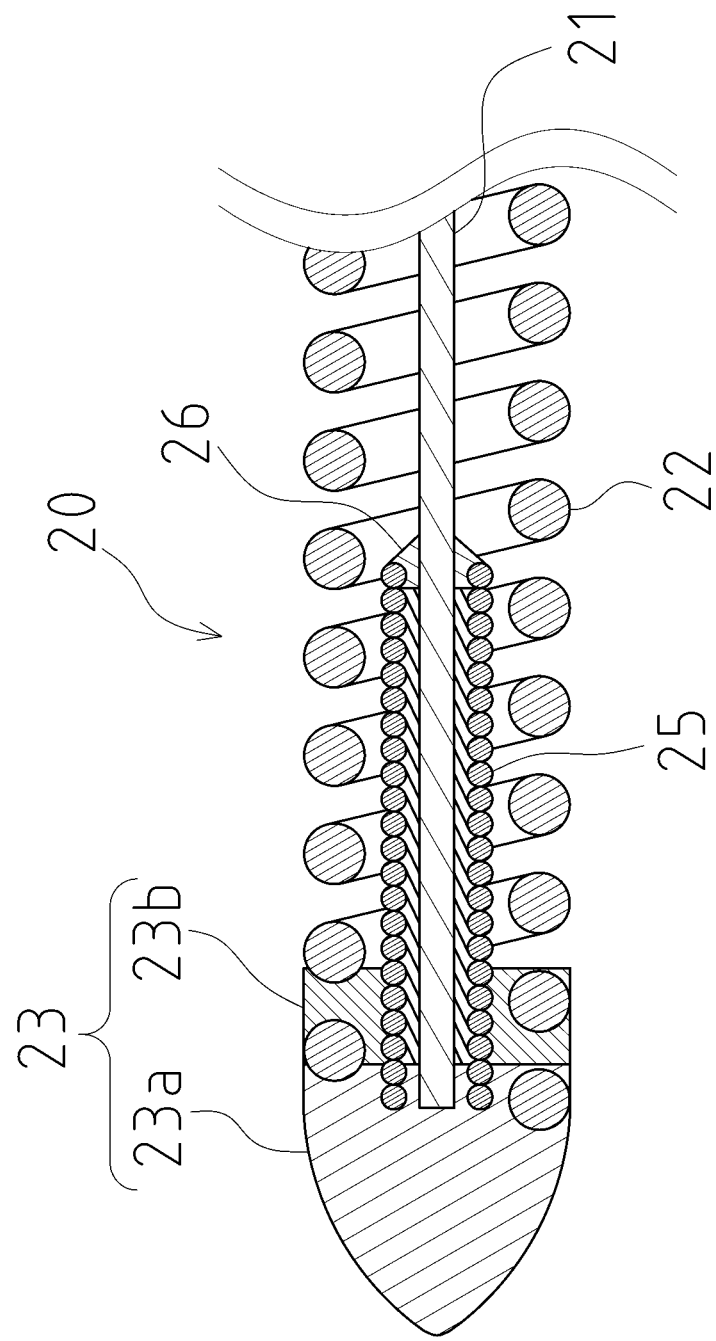
FIG. 3 is an explanatory view of a structure of a distal part of a guidewire according to the disclosed embodiments.

FIG. 3 is an explanatory view of a structure of a distal part of a guidewire 20 according to a modification. The guidewire 20 of the modification is different from the guidewire 10 of FIGS. 1 and 2 in the following respects. The guidewire 20 of the modification includes an inner coil 25 between an outer coil 22 and a core shaft 21. The inner coil 25 in the guidewire 20 of this modification has no gap between its elemental wires (a so-called closely wound coil). The closely wound inner coil 25 includes a closely wound single-strand coil, a closely wound coil formed by winding a plurality of elemental wires in a helical fashion, or the like.

As shown in FIG. 3, a second brazing member 23b of a distal-end brazing member 23 does not reach the core shaft 21. In other words, the second brazing member 23b is provided between the outer coil 22 and the inner coil 25 but is not provided between the inner coil 25 and the core shaft 21.

As for other points, the guidewire 20 of the modification is the same as the guidewire 10 of FIGS. 1 and 2. Therefore, a brazing material forming a first brazing member 23a has a melting point higher than a melting point of a brazing material forming the second brazing member 23b. Examples of combinations of a brazing material C forming the first brazing member 23a and a brazing material D forming the second brazing member 23b are the same as the various combinations explained above for the guidewire 10 of FIGS. 1 and 2.

A proximal end of the inner coil 25 and the core shaft 21 are joined to each other with a middle brazing member 26.

Also in the guidewire 20, because the melting point of the first brazing member 23a is higher than the melting point of the second brazing member 23b, the first brazing member 23a at the distal-most end retains its desired shape reliably even when the first brazing member 23a and the second brazing member 23b are formed, for example, for reasons related to procedures in assembling the guidewire 20.

In addition, in the guidewire 20, the second brazing member 23b is thus provided between the outer coil 22 and the inner coil 25 but is not provided between the inner coil 25 and the core shaft 21, and, as a result, the amount of the brazing material used for forming the second brazing member 23b is reduced. For this reason, along with the relationship that the melting point of the first brazing member 23a is higher than the melting point of the second brazing member 23b, deformation of the first brazing member 23a due to a heat produced during formation of the second brazing member 23b is prevented more reliably.

Figure 4:
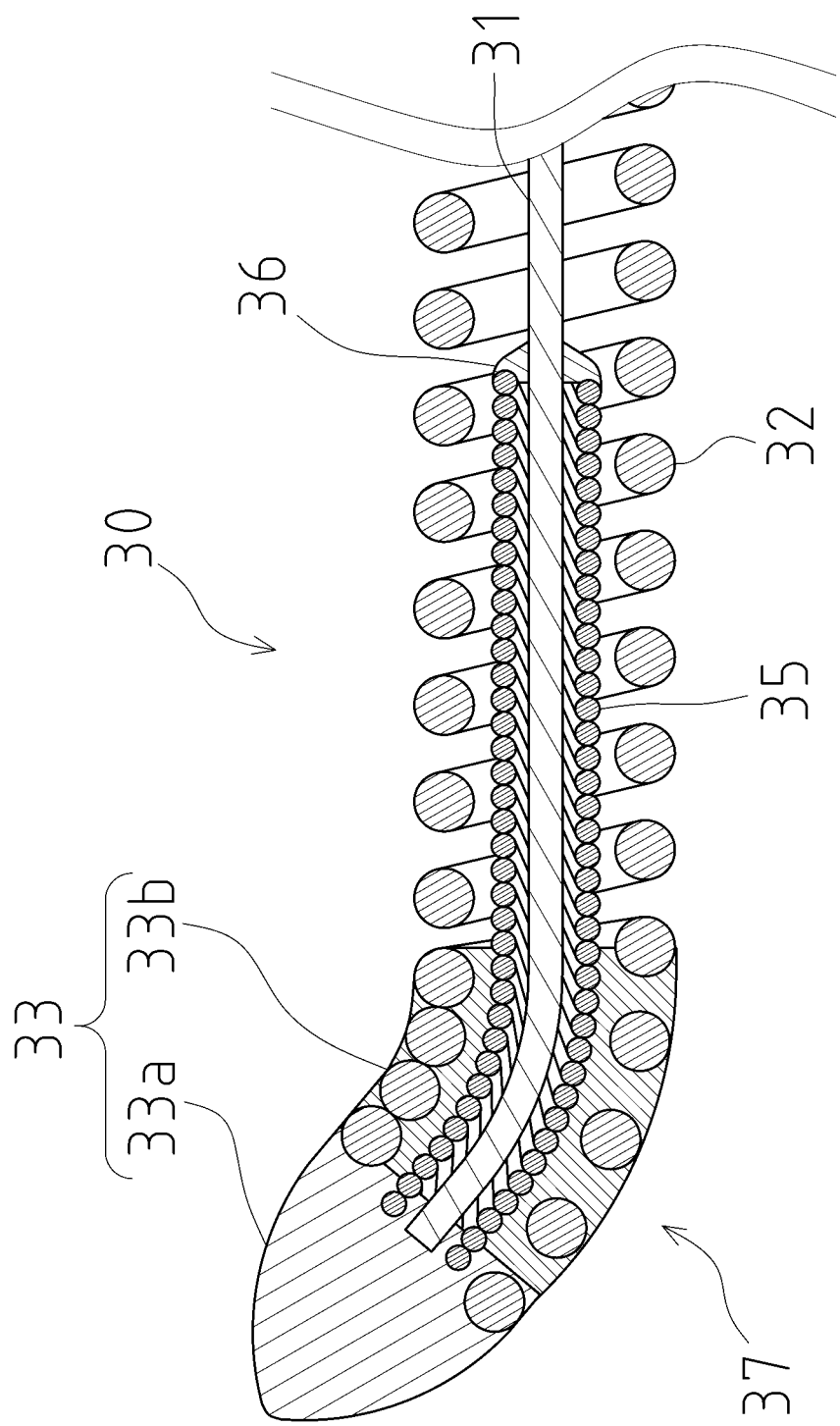
FIG. 4 is an explanatory view of a structure of a distal part of a guidewire according to the disclosed embodiments.

FIG. 4 is an explanatory view of the structure of a distal part of a guidewire 30 according to another modification. The guidewire 30 of FIG. 4 is different from the guidewire 20 of FIG. 3 in the following respects. The distal part of the guidewire 30 includes a curved part 37. In addition, a second brazing member 33b of a distal-end brazing member 33 is provided in the curved part 37.

As for other points, the guidewire 30 of FIG. 4 is the same as the guidewire 20 of FIG. 3. The guidewire 30 includes a core shaft 31, and an outer coil 32 and an inner coil 35 that surround an outer periphery of the core shaft 31. A brazing material forming a first brazing member 33a of the distal-end brazing member 33 has a melting point higher than a melting point of a brazing material forming the second brazing member 33b. Examples of combinations of a brazing material E forming the first brazing member 33a and a brazing material F forming the second brazing member 33b are the same as the various combinations explained above for the guidewire 10 of FIGS. 1 and 2.

The proximal end of the inner coil 35 and the core shaft 31 are joined to each other with a middle brazing member 36.

In FIG. 4, as in the case of the guidewire 20 of FIG. 3, the second brazing member 33b is provided between the outer coil 32 and the inner coil 35 but is not provided between the inner coil 35 and the core shaft 31 (see FIG. 4). Another configuration, in which no inner coil 35 is provided and the second brazing member 33b is provided between the outer coil 32 and the core shaft 31 in the curved part 37, may also be adopted (not shown in the figures).

However, providing the second brazing member 33b between the outer coil 32 and the inner coil 35 in the curved part 37 as in FIG. 4 is preferable, because the amount of the brazing material used for forming the second brazing member 33b is reduced, and an influence of heat on the first brazing member 33a is reduced as a result.

In the guidewire 30, the presence of the second brazing member 33b in the curved part 37 enables retention of the curved shape of the guidewire 30.

In addition, even though the second brazing member 33b is provided in order to retain the curved shape of the guidewire 30, the first brazing member 33a still retains its desired shape because the melting point of the brazing material forming the first brazing member 33a is higher than the melting point of the brazing material forming the second brazing member 33b.

Thus, the guidewire 30 of FIG. 4 simultaneously retains the desired curved shape of the guidewire 30 and the desired shape of the first brazing member 33a at the distal-most end.

Although guidewires of the disclosed embodiments are explained above, the present invention is not limited to these embodiments. For example, the inner coil 25 of the guidewire 20 according to FIG. 3, which is described as a closely wound coil, may be a loosely wound coil instead (a coil having its elemental wires not in contact with each other and having gaps between the elemental wires).

However, when the inner coil 25 is a closely wound coil, penetration of the brazing material into the space between the inner coil 25 and the core shaft 21 is effectively prevented in a process of forming the second brazing member 23b, and the amount of the brazing material used for forming the second brazing member 23b is reduced. Therefore, with consideration given to the influence of heat on the first brazing member 23a at the time of forming the second brazing member 23b, the inner coil 25 is preferably a closely wound coil.

What is claimed is:

1. A guidewire comprising:
a core shaft,
a closely wound inner coil surrounding an outer periphery of the core shaft,
a loosely wound outer coil surrounding an outer periphery of the closely wound inner coil,
a first brazing member that joins a distal end of the core shaft, a distal end of the closely wound inner coil, and a distal end of the loosely wound outer coil, and
a second brazing member provided adjacent to and on a proximal side of the first brazing member, and provided between the loosely wound outer coil and the closely wound inner coil but not between the closely wound inner coil and the core shaft,
wherein:
a melting point of the first brazing member is higher than a melting point of the second brazing member, and
an empty annular space is formed between the inner and outer coils, wherein the empty annular space extends from the second brazing member to a proximal terminal end of the closely wound inner coil.

2. The guidewire according to claim 1, wherein the first brazing member is formed of a brazing material containing gold, silver and tin.

3. The guidewire according to claim 2, wherein the second brazing member is formed of a gold-tin brazing material.

4. The guidewire according to claim 2, wherein the second brazing member is formed of a silver-tin brazing material.

5. The guidewire according to claim 2, wherein:
a distal part of the guidewire includes a curved part, and
the second brazing member is provided in the curved part.

6. The guidewire according to claim 1, wherein:
a distal part of the guidewire includes a curved part, and
the second brazing member is provided in the curved part.

7. The guidewire according to claim 1, wherein the first brazing member is provided among the loosely wound outer coil, the closely wound inner coil, and the core shaft.

8. The guidewire according to claim 1, wherein the loosely wound outer coil is wound loosely over an entire length of the closely wound inner coil.

* * * * *